United States Patent [19]

Brazdil, Jr. et al.

[11] Patent Number: 4,746,753

[45] Date of Patent: May 24, 1988

[54] PREPARATION OF ACRYLONITRILE FROM PROPYLENE, OXYGEN AND AMMONIA IN THE PRESENCE OF AN ALKALI METAL PROMOTED BISMUTH, CERIUM, MOLYBDENUM, TUNGSTEN CATALYST

[75] Inventors: James F. Brazdil, Jr., Lyndhurst; Dev D. Suresh, Macedonia; Robert K. Grasselli, Chagril Falls, all of Ohio

[73] Assignee: The Standard Oil Company, Cleveland, Ohio

[21] Appl. No.: 880,657

[22] Filed: Jul. 1, 1986

Related U.S. Application Data

[63] Continuation of Ser. No. 258,708, Apr. 29, 1981, abandoned.

[51] Int. Cl.$^4$ ............................................. C07C 120/14
[52] U.S. Cl. .................................. 558/324; 558/321; 558/322; 568/477; 568/478; 568/479; 585/630
[58] Field of Search ....................... 558/321, 322, 324

[56] References Cited

U.S. PATENT DOCUMENTS 3,173,957 3/1965 McDaniel et al. ............ 260/465.3 X
3,262,962 7/1966 McDaniel et al. ............... 260/465.3
3,316,182 4/1967 McDaniel et al. .................. 252/451
3,415,886 12/1968 McClellan .................... 260/465.3 X
3,541,129 11/1970 Yamada et al. .................. 260/465.3
3,833,638 9/1974 Knox et al. ...................... 260/465.3
3,907,859 9/1975 Grasselli et al. ................. 260/465.3
3,993,680 11/1976 Grasselli et al. ................. 260/465.3
4,162,234 7/1979 Grasselli et al. ............. 260/465.3 X
4,167,494 9/1979 Grasselli et al. ............. 260/465.3 X
4,174,354 11/1979 Grasselli et al. ............. 260/465.3 X

FOREIGN PATENT DOCUMENTS 1034597 7/1978 Canada .
2403716 8/1974 Fed. Rep. of Germany ... 260/465.3
1445512 1/1973 United Kingdom .

OTHER PUBLICATIONS

C.A., 92:42592z (1980), Otaki et al.

Primary Examiner—Joseph Paul Brust
Attorney, Agent, or Firm—M. F. Esposito; J. E. Miller; L. W. Evans

[57] ABSTRACT

Bismuth cerium molybdate catalysts promoted with alkali metal and other optional ingredients provide high yields of acrylonitrile in the ammoxidation of propylene.

3 Claims, No Drawings

PREPARATION OF ACRYLONITRILE FROM PROPYLENE, OXYGEN AND AMMONIA IN THE PRESENCE OF AN ALKALI METAL PROMOTED BISMUTH, CERIUM, MOLYBDENUM, TUNGSTEN CATALYST

BACKGROUND OF THE INVENTION

This is a file wrapper continuation of application Ser. No. 258,708, filed Apr. 29, 1981, now abandoned.

The present invention relates to new catalyst systems for ammoxidizing propylene to produce acrylonitrile and for carrying out other oxidation-type reactions such as the oxidation of unsaturated olefins to produce the corresponding aldehydes and acids and the oxydehydrogenation of various olefins to produce diolefins.

The catalytic ammoxidation of propylene to produce acrylonitrile is a well known process. Many different catalysts have been proposed for this process. While such catalysts are capable of providing excellent yields of acrylonitrile, it is always desirable to provide new catalysts especially effective in this reaction.

Accordingly, it is an object of the present invention to provide new catalysts which are especially useful in the ammoxidation of propylene to produce acrylonitrile.

In addition, it is a further object of the present invention to provide new catalysts which are also useful in other oxidation-type reactions such as the oxidation of acrolein and methacrolein to produce the corresponding unsaturated aldehydes and acids and the oxydehydrogenation of various olefins such as isoamylenes to produce the corresponding diolefins such as isoprene.

SUMMARY OF THE INVENTION

These and other objects are accomplished by the present invention which is based on the discovery that the incorporation of certain elements into known bismuth cerium molydate redox catalysts remarkably exhances the catalytic properties of such catalysts for use in various oxidation-type reactions such as the ammoxidation of propylene to produce acrylonitrile.

Thus, the present invention provides an improvement in known bismuth cerium molybdate redox catalysts wherein a promoting amount of an alkali metal, Tl, Sm, Ag, Cu, Cr, Sb, rare earth other than Ce and Sm, Te, Ti, Zr, Th or mixture thereof is incorporated into the catalyst.

In addition, the present invention provides an improvement in the known process for ammoxidizing propylene to produce acrylonitrile by contacting propylene, ammonia and molecular oxygen with a bismuth cerium molybdate oxidation catalyst at an elevated temperature, the improvement wherein at least one of the above-noted promoter elements are incorporated into the catalyst.

DETAILED DESCRIPTION

Catalysts

Bismuth cerium molybdate redox catalysts are known. See, for example, the McDaniel and Young patents, U.S. Pat. Nos. 3,173,957, 3,262,962 and 3,316,182, the disclosures of which are incorporated herein by reference. In accordance with the invention it has been found that the incorporation of certain additional elements into such catalysts will improve the catalytic properties of these materials. Usually this improvement will be reflected in an increase in product yields, which is a measure of the amount of product produced based on the amount of reactant fed. In some instances, however, this improvement will be reflected in an increase in product selectivity, which is a measure of the ability of the catalyst to preferentially form the desired product as opposed to unwanted byproducts. In any event, incorporation of one or more of these elements, either by adding such elements to a known bismuth cerium molybdate base system or substituting these elements for a part of the bismuth and/or cerium in the known base system, will provide a catalyst with better catalytic properties than the corresponding base system. Furthermore, catalysts of the invention produce by-product effluents with very low chemical oxidation demand (COD) and are thus environmentally superior to many known redox catalysts such as the iron bismuth molybdates.

The elements found to be effective promoters in accordance with the invention are (1) Sm or a monovalent element such as alkali metals, Tl, Ag and Cu, preferably K, Rb and/or Cs, (2) elements whose most common valence state is 4+, e.g. Te, Ti, Zr and Th, and (3) Cr, Sb and rare earths other than Ce and Sm, such as La, Y, Pr, Nd and Di. These elements can be incorporated into the bismuth cerium molybdate base systems alone or in mixtures.

The catalysts of the invention correspond to the following general formula

wherein
A is alkali metal, Tl, Sm, Ag, Cu or mixtures thereof, preferably K, Rb, Cs or mixtures thereof,
Q is Ti, Zr, Th, Te or mixtures thereof,
R is Cr, Sb or a rare earth element other than Sm and Ce, preferably La, Y, Pr, Nd, Di or mixtures thereof, and
wherein
a is 0 to 6,
b is 0.01 to 24,
c is 0.01 to 24,
$0 \leq d+e \leq f$,
$d+e+f$ is 8 to 16,
q is 0 to 24,
r is 0 to 24,
$a+q+r>0$
x is a number sufficient to satisfy the valence requirements of the other elements present,
said catalyst being free of iron and the combination of A and Te.

Preferred catalysts are those in which $a+q+r \leq b+c+2$. Also preferred are catalysts which satisfy the relationship $2d+2e+2-f=a+3b+3c+4q+3r\pm z$ wherein $z \leq 10$, preferably $z \leq 4$. Of these, those in which $a>0$ are especially preferred.

In this regard, catalysts of special interest are those containing Sm or a monovalent promoter, i.e. an A element and optionally Cr and/or Sb. These catalysts can be defined by the formula:

wherein
A is alkali metal, Tl, Sm, Ag, Cu or mixtures thereof, preferably K, Rb, Cs or mixture thereof; and R=Cr and/or Sb
wherein
a is greater than zero to 6;
b is 0.01 to 24;
c is 0.01 to 24;
r is 0 to 12
$0 \leq d+e \leq f$;
$d+e+f=8$ to 16; and
x is a number sufficient so that the valence requirements of the other elements present are satisfied.

Preferred catalysts of this type are those in which $b+c \leq f+d+e$, more preferably those which satisfy the relation $$\frac{1}{2} \leq \frac{b+c}{f+d+e} \leq \frac{5}{6}$$

Of these catalysts even more preferred are those in which
$d+e+f=12$ to 12.5;
a is 0.01 to 2;
b is 1 to 11; and
c is 1 to 11.
r is 0 to 5

Still more preferred are those of the above catalysts in which a is 0.02 to less than 0.3, preferably 0.02 to 0.2.

Another interesting group of catalysts containing the monovalent A promoter is those of the above formula (2) which satisfy the relation $2d+2e+2f=a+3b+3c+3r\pm z$, wherein $z \leq 6$, preferably $\leq 2$.

The above formulas in general describe the catalysts produced by the invention. However, as will be appreciated by those skilled in the art, such formula descriptions do not connote that every material following therein will exhibit superior effectiveness as a catalyst. Rather such descriptions connote only that catalysts of the invention will have compositions corresponding to the above formulas. Those skilled in the art readily understand that a catalyst in order to exhibit good catalytic properties must have an appropriate balance of ingredients and that too much of any one element can drastically reduce its effectiveness or even inactivate the catalyst. The same considerations apply to this invention. The base catalyst systems must be compounded so as to have an appropriate balance of ingredients for catalyzing the specific reaction of interest. In addition, the exact amount of A, R or Q promoter element to be incorporated therein, either by adding the promoter to the existing system or substituting some of the Bi and/or Ce content of the base system with promoter, must also be appropriately selected. In accordance with the invention, the incorporation of the above-described A, R and Q elements into known bismuth cerium molybdate catalysts will exhibit a promoting effect on the catalysts in various oxidation-type reactions. Those skilled in the art can easily determine how much of a particular A, Q or R element should be incorporated into a particular bismuth cerium molybdate base system to promote a particular oxidation-type reaction by simple routine experimentation, especially in view of the following working examples.

Also, it has been found that some combinations of A, Q and R elements do not result in catalyst improvements but may indeed drastically reduce catalyst effectiveness. For example, the inclusion of even very small amounts of potassium in a tellurium-containing catalyst will essentially inactivate the catalyst. Obviously, such combinations should also be avoided. Accordingly, the catalysts of the invention should be free of the combination of tellurium with any of the A elements, i.e. alkali metals, Tl, Sm, Ag and Cu.

The catalysts of the invention, at least in its preferred embodiment, are essentially single-phase systems being isostructural with lanthanum molybdate ($La_2MO_3O_{12}$). See W. Jeitschko, Acta. Cryst. B29, 2074 (1973). They are therefore different from the known iron bismuth molybdates which are multi-phase materials.

The catalysts of the invention can be used either in unsupported form or supported on suitable carriers such as $SiO_2$, $Al_2O_3$, $BPO_4$, $SbPO_4$, $ZrO_2$, $TiO_2$, Alundum and the like. The catalysts can also be coated on these supports by special techniques known in the art.

These catalysts can be prepared by conventional techniques such as disclosed in Grasselli, et al., U.S. Pat. No. 3,642,930. These catalysts are most easily prepared by slurry techniques wherein an aqueous slurry containing all of the elements in the objective catalyst is produced, the water removed from the aqueous slurry to form a precatalyst precipitate or powder and the precatalyst then heated in the presence of an oxygen-containing gas such as air at elevated temperature to calcine the precatalyst thereby forming the catalyst. Liquids other than water, such as $C_1$ to $C_8$ alcohols can also be used to form the precatalyst slurry.

Ammoxidation

The catalysts of the invention find significant use in the ammoxidation of propylene to produce acrylonitrile. This reaction is well known and described, for example, in the above-noted Grasselli, et al. patent. In general, the ammoxidation reaction is accomplished by contacting the reactant, oxygen and ammonia with a particular catalyst in the vapor phase. The inventive reaction is carried out in the same manner and under the conditions generally set forth in these patents.

In a preferred aspect, the inventive process comprises contacting a mixture comprising propylene, ammonia and oxygen with the catalyst of this invention at an elevated temperature and at atmospheric or near atmospheric pressure.

Any source of oxygen may be employed in this process. For economic reasons, however, it is preferred that air be employed as the source of oxygen. From a purely technical viewpoint, relatively pure molecular oxygen will give similar results. The molar ratio of oxygen to the olefin in the feed to the reaction vessel should be in the range of 0.5:1 to 4:1 and a ratio of about 1:1 to 3:1 is preferred.

Low molecular weight saturated hydrocarbons do not appear to influence the reaction to an appreciable degree, and these materials can be present; consequently, the addition of saturated hydrocarbons to the reaction feed is contemplated within the scope of this invention. Likewise, diluents, such as nitrogen and the oxides of carbon, may be present in the reaction mixture without deleterious effect.

The molar ratio of ammonia to olefin in the feed to the reactor may vary between about 0.05:1 to 5:1. There is no real upper limit for the ammonia/olefin ratio, but there is generally no reason to exceed the 5:1 ratio. At ammonia/olefin ratios appreciably less than the stoichiometric ratio of 1:1, various amounts of oxygenated derivatives of the olefin will be formed.

Significant amounts of unsaturated aldehydes, as well as nitriles, will be obtained at ammonia-olefin ratios substantially below 1:1, i.e. in the range of 0.15:1 to 0.75:1. Above the upper limit of this range, the amount of aldehydes produced rapidly decreases. Within the ammonia-olefin range stated, maximum utilization of ammonia is obtained and this is highly desirable. It is generally possible to recycle any unreacted olefin and unconverted ammonia.

Water can also be included in the feed although it is not essential. In some instances, e.g. fixed-bed systems, water may improve the selectivity of the reaction and the yield of nitrile. However, reactions not including water in the feed are within the scope of the present invention and are preferred in the fluid-bed operation.

In general, the molar ratio of added water to olefin, when water is added, is in the neighborhood of 0.1:1 or higher. Ratios on the order of 1:1 to 6:1 are particularly desirable, but higher ratios may be employed, i.e. up to about 10:1.

The reaction is carried out at an elevated temperature such as 200° to 600° C., preferably 400° C. to 550° C., more preferably 420° C. to 500° C. The reaction should be carried out at about atmospheric or slightly above atmospheric (2 to 3 atmospheres) pressure. In general, high pressures, i.e. above 15 atmospheres, are not suitable since higher pressures tend to favor the formation of undesirable byproducts.

The apparent contact time is not critical, and contact times in the range of from 0.1–40 seconds may be employed. The optimal contact time will, of course, vary depending upon the reactant being used, but in general, contact time of from 1–15 seconds is preferred.

The inventive ammoxidation reaction is carried out in the vapor phase. Normally, the process is conducted on a continuous basis using either a fixed-bed or a fluid-bed catalyst. However, a batch operation can be employed.

The reaction product passing out of the reactor is normally in the form of a vapor. Conventionally, this gaseous reaction product is treated to remove $NH_3$ and then partially condensed either by indirect contact with a cooling medium or direct contact with water to form a liquid phase containing acrylonitrile, acrolein, acrylic acid, HCN and acetonitrile and a vapor phase containing $CO_2$, CO, $N_2$ and $O_2$. The acrylonitrile is then separated from the liquid phase by a number of different techniques such as, for example, distillation or water extraction/distillation. Additional steps can be employed to separately recover HCN and/or acetonitrile from the gross reaction product.

In addition to propylene, other hydrocarbons and oxygenated hydrocarbons can be ammoxidized with the catalysts of the invention. For example, alcohols such as isopropanol, n-propanol, t-butyl alcohol, and aldehydes such as acrolein and methacrolein can be readily converted to nitriles in accordance with the present invention. In addition to propylene, other preferred starting materials are aldehydes and alcohols containing three or four carbon atoms. The general ammoxidation process for converting olefins, alcohols and aldehydes to nitrile is well known and described for example in U.S. Pat. No. 3,456,138, the disclosure of which is incorporated herein by reference.

Oxidation

The catalysts of this invention can also be employed in the catalyst oxidation of olefins to various different reaction products.

The reactants used in the oxidation to oxygenated compounds are oxygen and an olefin such as propylene, isobutylene and other olefins having up to three contiguous carbon atoms (i.e. three carbon atoms arranged in a straight chain). Instead of olefins, alcohols such as isopropanol, n-propanol or tert-butanol can be used as reactants.

The olefins or alcohols may be in admixture with paraffinic hydrocarbons, such as ethane, propane, butane and pentane. For example, a propylene-propane mixture may constitute the feed. This makes it possible to use ordinary refinery streams without special preparation.

The temperature at which this oxidation is conducted may vary considerably depending upon the catalyst, the particular olefin being oxidized and the correlated conditions of the rate of throughput or contact time and the ratio of olefin to oxygen. In general, when operating at pressures near atmospheric, i.e. 0.1 to 10 atmospheres, temperatures in the range of 150° to 600° C. may be advantageously employed. However, the process may be conducted at other pressures, and in the case where superatmospheric pressures, e.g. above 5 atmospheres are employed, somewhat lower temperatures are possible. In the case where this process is employed to convert propylene to acrolein, a temperature range of 200° to 500° C. has been found to be optimum at atmospheric pressure.

While pressures other than atmospheric may be employed, it is generally preferred to operate at or near atmospheric pressure, since the reaction proceeds well at such pressures and the use of expensive high pressure equipment is avoided, and formation of undesired byproducts and waste is diminished.

The apparent contact time employed in the process is not critical and it may be selected from a broad operable range which may vary from 0.1 to 50 seconds. The apparent contact time may be defined as the length of time in seconds which a unit volume of gas measured under the conitions of reaction is in contact with the apparent unit volume of the catalyst. It may be calculated, for example, from the apparent volume of the catalyst bed, the average temperature and pressure of the reactor, and the flow rates of the several components of the reaction mixture.

The optimum contact time will, of course, vary depending upon the olefin being treated, but in the case of propylene and isobutylene, the preferred contact time is 0.15 to 15 seconds.

A molar ratio of oxygen to olefin between about 0.5:1 to 5:1 generally gives the most satisfactory results. For the conversion of propylene to acrolein, a preferred ratio of oxygen to olefin is from about 1:1 to about 2.5:1. The oxygen used in the process may be derived from any source; however, air is the least expensive source of oxygen and is preferred for that reason.

The addition of water to the reaction mixture in oxidation reactions can have a beneficial influence on the conversion and yields of the desired product especially in fixed-bed reactions. The manner in which water affects the reaction is not fully understood. In any event, it is preferred in fixed-bed operation to include water in the reaction mixture, and in general a ratio of olefin to water in the reaction mixture of from 1:0.25 to 1:10 will give very satisfactory results while a ratio of 1:0.5 to 1:6 has been found the optimum when converting propylene to acrolein.

Inert diluents such as oxygen and carbon dioxide may be present in the reaction mixture.

Oxydehydrogenation

In accordance with the present invention, the catalyst system of the present invention can also be employed in the catalytic oxidative dehydrogenation of olefins to diolefins and aromatic compounds. In this process, the feed stream in vapor form containing the olefin to be dehydrogenated and oxygen is conducted over the catalyst at a comparatively low temperature to obtain the corresponding diolefin.

By the term "olefin" as used herein is meant open chain as well as cyclic olefins. The olefins dehydrogenated in accordance with this invention have at least four and up to about nine nonquanternary carbon atoms, of which at least four are arranged in series in a straight chain or ring. The olefins preferably are either normal straight chain or tertiary olefins. Both cis and trans isomers, where they exist, can be dehydrogenated.

Among the many olefinic compounds which can be dehydrogenated in this way are butene-1; butene-2; pentene-1; pentene-2; pentenes, hexenes, etc. such as 2-methylbutene-1, 2-methylbutene-2, 3-methylbutene-1, 2-methylpentene-1, 3-methylpentene-2, 4-methylpentene-2; heptene-1; 3,4-dimethyl-pentene-1; octene-1; cyclopentene; cyclohexene, 3-methyl cyclohexene and cycloheptene.

Open chain olefins yield diolefins, and, in general, six-membered ring olefins yield aromatic ring compounds. The higher molecular weight open chain olefins may cyclize to aromatic ring compounds.

The feed stock in addition to the olefin and oxygen can contain one or more paraffins or naphthenic hydrocarbons having up to about ten carbon atoms, which may be present as impurities in some petroleum hydrocarbon stocks and which may also be dehydrogenated in some cases.

The amount of oxygen can be within the range of from about 0.3 to about 4 moles per mole of double-bond created. Stoichiometrically, 0.5 mole of oxygen is required for the dehydrogenation of one mole of monolefin to a diolefin. It is preferred to employ an excess of oxygen, e.g. an oxygen/olefin ratio of from 0.6 to about 3, in order to ensure a higher yield of diolefin per pass. The oxygen can be supplied as pure or substantially pure oxygen or as air.

When pure oxygen is used, it may be desirable to incorporate a diluent in the mixture such as steam, carbon dioxide or nitrogen.

The feed stock can be catalytically dehydrogenated in the presence of steam, but this is not essential. When steam is used, from about 0.1 to about 6 moles of steam per mole of olefin reactant is employed, but amounts larger than this can be used.

The dehydrogenation proceeds at temperatures within the range of from about 200° to 800° C. Optimum yields are obtainable at temperatures within the range from about 300° to 600° C.

The preferred reaction pressure is approximately atmospheric, within the range of from about 0.1 to about 5 atmospheres.

Only a brief contact time with the catalyst is required for effective oxydehydrogenation. The apparent contact time with the catalyst can vary from about 0.1 up to about 50 seconds but higher contact times can be used if desired. At the short contact times, comparatively small reactors and small amounts of catalyst can be used effectively.

Process Conditions

In carrying out the foregoing processes, any apparatus of the type suitable for carrying out the oxidation reactions in the vapor phase may be employed. The processes may be conducted either continuously or intermittently. The catalyst may be a fixed-bed employing a particulate or pelleted catalyst or, in the alternative, a fluid-bed catalyst may be employed which is normally micro-spheroidal.

WORKING EXAMPLES

In order to more thoroughly describe the present invention, the following working examples are presented. In these examples, the following definitions apply:

"Yield" means $\frac{\text{moles product formed}}{\text{moles reactant fed}} \times 100$ "Selectivity" means $\frac{\text{moles product formed}}{\text{moles reactant reacted}} \times 100$ In each of the examples and comparative example, a catalyst having the composition set forth in the following tables was prepared in accordance with a standard laboratory preparation. For example, the catalyst of Examples 1 to 3 was prepared as follow:

42.55 gms. of ammonium heptamolybdate was dissolved in about 100 ml. of distilled water. To this was added 41.59 gms. of a 40% silica sol. In a separate beaker, 38.81 gms. of $Bi(NO_3)_{3.5}$ $H_2O$, 43.86 gms. of $(NH_4)_4Ce(NO_3)_6$ and 0.20 gms. $KNO_3$ were dissolved in 10% aqueous nitric acid. The metal nitrate solution was then slowly added to the ammonium heptamolybdate/silica sol mixture along with approximately 50 ml. of distilled water and the pH of the mixture was adjusted to 3.0 by the addition of concentrated $NH_4OH$. The mixture was then refluxed for 3 hours. After approximately 30 minutes of refluxing, the mixture began to thicken and accordingly an additional 150 ml. of distilled water was added. After refluxing, the mixture was evaporated to dryness on a hotplate, dried at 120° C. for 16 hours and then calcined at 290° C. for 3 hours and then at 425° C. for 3 hours. The partially calcined catalyst was then ground, screened to 25 to 35 mesh and then calcined at 550° C. for 16 hours to produce the desired catalyst.

EXAMPLES 1 to 10 and COMPARATIVE EXAMPLES A to C

Eights catalysts of the invention and three comparative catalysts were tested in the known ammoxidation reaction for producing acrylonitrile from propylene. In each example and comparative example, 5 cc. of the catalyst was charged into a 6 cc. reactor and contacted with a feed comprising 1 propylene/1.1 $NH_3$/10.6 air/4 $H_2O$ at elevated temperature for a contact time of 3 seconds. The gross reaction product recovered from each experiment was then analyzed.

The composition of the catalysts, the reaction temperatures and the results obtained are set forth in the following Table 1.

TABLE 1

Ammoxidation of Propylene

Feed: 1 propylene/1.1 $NH_3$/10.6 air/4 $H_2O$
Contact Time: 3 seconds
Catalyst Support: 20% $SiO_2$

| Ex No | Catalyst Composition | Temp (C.) | Propy Conv | Selec to AN | AN Yield (%) | HCN Yield (%) |
|---|---|---|---|---|---|---|
| 1 | $K_{0.1}Bi_4Ce_4Mo_{12.05}O_x$ | 430 | 83.6 | 78.4 | 65.5 | 3.1 |
| 2 | $K_{0.1}Bi_4Ce_4Mo_{12.05}O_x$ | 445 | 92.8 | 81.5 | 75.6 | 3.3 |
| 3 | $K_{0.1}Bi_4Ce_4Mo_{12.05}O_x$ | 460 | 99.3 | 80.4 | 79.8 | 3.1 |
| 4 | $K_{0.05}Cs_{0.02}Bi_4Ce_4Mo_{12.03}O_x$ | 460 | 95.2 | 82.5 | 78.5 | 2.5 |
| 5 | $Tl_{0.03}Bi_4Ce_4Mo_{12}O_x$ | 460 | 98.8 | 80.3 | 79.3 | 3.4 |
| 6 | $Cs_{0.02}Bi_4Ce_4Mo_{12}O_x$ | 445 | 98.4 | 75.6 | 74.4 | 3.6 |
| 7 | $K_{0.1}Bi_9Ce_1Mo_{12}O_x$ | 460 | 95.5 | 83.0 | 79.3 | 2.5 |
| 8 | $K_{0.05}Bi_4Ce_4W_2Mo_{10}O_x$ | 460 | 98.5 | 81.8 | 80.5 | 3.1 |
| A | $Bi_4Ce_4Mo_{12}O_x$ | 430 | 100.0 | 65.8 | 65.8 | 3.0 |
| B | $Bi_4Ce_4Mo_{12}O_x$ | 460 | 100.0 | 71.5 | 71.5 | 2.9 |
| C | $Bi_4Ce_4W_2Mo_{10}O_x$ | 430 | 98.6 | 70.5 | 69.5 | 3.5 |
| D | $Bi_9Ce_1Mo_{12}O_x$ | 460 |  | 75.7 | 71.9 | 3.1 |
| 9 | $Cs_{0.04}Bi_4Ce_4W_4Mo_8O_x$* | 460 | 99.5 | 82.2 | 81.8 | 3.1 |
| 10 | $Cs_{0.05}Bi_4Ce_4W_2Mo_{12}$* | 460 | 96.5 | 81.6 | 78.8 | 2.8 |
| 11 | $Cs_{0.04}Bi_4Ce_4Sb_1W_2Mo_{10}O_x$* | 460 | 97.9 | 81.7 | 80.0 | 2.0 |

*Catalyst contained 50% $SiO_2$ and was calcined at 650° C.

From the foregoing, it can be seen that the inventive catalysts provide significant yelds of acrylonitrile when used in the conventional ammoxidation reaction, Thus, these catalysts are of significant commercial interest in this field. Moreover, these catalysts are also advantageous because they are redox stable and they provide an environmentally acceptable effluent (i.e. a byproduct effluent with a very low COD).

Comparative Examples E

Example 3 was repeated except that the bismuth content of the catalyst was replaced with tellurium. The results obtained, as well as the results of Example 3 and Comparative Example B, are set forth in the following Table 2.

TABLE 2

| Ex No | Catalyst (+20 SiO2) | Temp (C.) | AN Yield (%) | Selec to AN |
|---|---|---|---|---|
| B | $Bi_4Ce_4Mo_{12}O_x$ | 460 | 71.5 | 71.5 |
| 3 | $K_{0.1}Bi_4Ce_4Mo_{12}O_x$ | 460 | 79.8 | 80.4 |
| E | $K_{0.1}Te_4Ce_4Mo_{12}O_x$ | 460 | 10.4 | 24.2 |

The above table shows that the addidtion of alkali metal to the known bismuth cerium molybdate catalyst significantly improves the ability of the catalyst to produce acrylonitrile. In addition, this table further shows that the addition of alkali metal to a corresponding tellurium cerium molybdate catalyst effectively inactivates the catalyst. Specifically, Example 3 and Comparative Example E show that bismuth and tellurium are not equivalent in this system.

EXAMPLES 12 to 29 and COMPARATIVE EXAMPLES F to H

Examples 1 to 10 were repeated using various different R and Q promoters of the invention. In these examples a portion of the cerium and/or bismuth was replaced with the R or Q element so that a stoichiometric balance with respect to molybdenum could be maintained. The results are set forth in the following Table 3.

TABLE 3

Ammoxidation of Propylene

Feed: 1 propylene/1.1 $NH_3$/10.6 air/4 $H_2O$
Contact Time: 3 seconds
Catalyst Support: 20% $SiO_2$

| Ex No | Catalyst Composition | Temp (C.) | Propy Conv | Selec to AN | AN Yield (%) | HCN Yield (%) |
|---|---|---|---|---|---|---|
| 12 | $Cr_2Ce_2Bi_4Mo_{12}O_x$ | 430 | 94.4 | 77.2 | 72.9 | 3.4 |
| 13 | $Cr_2Ce_2Bi_4Mo_{12}O_x$ | 445 | 98.6 | 74.9 | 73.8 | 3.6 |
| 14 | $K_{0.05}Cr_2Ce_2Bi_4Mo_{12.03}O_x$ | 460 | 89.5 | 77.6 | 69.4 | 2.6 |
| 15 | $Te_2Ce_2Bi_4Mo_{12}O_x$ | 430 | 98.9 | 72.2 | 71.4 | 3.4 |
| F | $K_{0.05}Te_2Ce_2Bi_4Mo_{12.03}O_x$ | 460 | 68.2 | 50.0 | 34.1 | 0.2 |
| 16 | $La_2Ce_2Bi_4Mo_{12}O_x$ | 430 | 98.7 | 67.3 | 66.4 | 3.1 |
| G | $La_4Bi_4Mo_{12}O_x$ | 430 | 94.6 | 56.0 | 53.0 | 3.7 |
| 17 | $K_{0.05}La_2Ce_2Bi_4Mo_{12.03}O_x$ | 430 | 93.4 | 77.5 | 72.4 | 3.0 |
| 18 | $K_{0.05}La_2Ce_2Bi_4Mo_{12.03}O_x$ | 445 | 98.1 | 77.1 | 75.6 | 3.0 |
| 19 | $K_{0.1}La_2Ce_2Bi_4Mo_{12.05}O_x$ | 430 | 75.4 | 83.8 | 63.2 | 3.0 |

TABLE 3-continued

Ammoxidation of Propylene

Feed: 1 propylene/1.1 NH$_3$/10.6 air/4 H$_2$O
Contact Time: 3 seconds
Catalyst Support: 20% SiO$_2$

| Ex No | Catalyst Composition | Temp (C.) | Propy Conv | Selec to AN | AN Yield (%) | HCN Yield (%) |
|---|---|---|---|---|---|---|
| 20 | K$_{0.1}$La$_2$Ce$_2$Bi$_4$Mo$_{12.05}$O$_x$ | 460 | 90.5 | 81.3 | 73.6 | 2.6 |
| 21 | K$_{0.1}$La$_4$Ce$_2$Bi$_2$Mo$_{12.05}$O$_x$ | 445 | 95.7 | 75.3 | 72.1 | 3.0 |
| 22 | K$_{0.1}$La$_4$Ce$_2$Bi$_2$Mo$_{12.05}$O$_x$ | 460 | 98.8 | 75.1 | 74.2 | 3.0 |
| 23 | K$_{0.1}$La$_6$Ce$_1$Bi$_1$Mo$_{12.05}$O$_x$ | 460 | 92.1 | 70.7 | 65.1 | 2.6 |
| 24 | Y$_2$Ce$_2$Bi$_4$Mo$_{12}$O$_x$ | 420 | 92.4 | 67.3 | 62.2 | 3.9 |
| 25 | K$_{0.05}$Y$_2$Ce$_2$Bi$_4$Mo$_{12.03}$O$_x$ | 460 | 98.7 | 76.3 | 75.3 | 2.8 |
| 26 | K$_{0.1}$Pr$_2$Ce$_2$Bi$_4$Mo$_{12.05}$O$_x$ | 460 | 94.7 | 76.2 | 72.1 | 6.9 |
| 27 | K$_{0.1}$Nd$_2$Ce$_2$Bi$_4$Mo$_{12.05}$O$_x$ | 460 | 97.6 | 75.8 | 74.0 | 2.9 |
| 28 | K$_{0.1}$Di$_2$Ce$_2$Bi$_4$Mo$_{12.05}$O$_x$ | 430 | 93.7 | 76.8 | 72.0 | 2.5 |
| 29 | Cr$_2$Ce$_3$Bi$_4$Mo$_{12}$O$_x$ | 430 | 98.7 | 68.4 | 67.5 | 2.7 |
| H | Cr$_2$Ce$_3$Te$_4$Mo$_{12}$O$_x$ | 430 | 46.0 | 75.5 | 34.7 | 0.5 |

From the above Table 3 it can be seen that the various R and Q elements set forth above also exert a promoting effect on bismuth cerium molybdate catalysts. In addition, it can be seen that alkali metal, specifically potassium, tends to decrease the activity (conversion) of catalysts but that this activity decline can be largely ameliorated by increasing the temperature without significant loss of acrylonitrile selectivity. However, even at very low concentrations, potassium essentially inactivates a tellurium containing catalyst in that not only is the activity of the catalyst significantly reduced but also its selectivity.

EXAMPLES 30, 31 and COMPARATIVE EXAMPLE I

A number of catalysts were used to ammoxidize propylene to produce acrylonitrile and a waste effluent, which was tested to determine chemical oxidation demand. In each example, the gross reactor effluent was scrubbed with aqueous sodium phosphate and the scrubber solution then vacuum distilled to remove acrylonitrile, HCN and acetonitrile. After diluting with water back to original volume, the scrubber solutions were analyzed for COD by a technique essentially the same as ASTM D1252. The compositions of the catalysts and the relative COD's obtained are set forth in the following Table 4. In this table, the COD a of the prior art iron bismuth molybdate catalyst is taken as 1.00 and the COD's of the other catalysts compared thereto.

TABLE 4

Relative Chemical Oxygen Demand

| Ex No | Catalyst Composition | Relative COD |
|---|---|---|
| I | 50% K$_{0.1}$Ni$_{2.5}$Co$_{4.5}$Fe$_3$BiP$_{0.5}$Mo$_{12}$O$_x$ + 50% SiO$_2$ | 1.00 |
| 30 | 50% Cs$_{0.04}$Bi$_4$Ce$_4$Mo$_8$W$_4$O$_x$ + 50% SiO$_2$ | 0.46 |
| 31 | 80% K$_{0.1}$Bi$_4$Ce$_4$Mo$_{12}$O$_x$ + 20% SiO$_2$ | 0.42 |

Table 4 shows that the catalysts of the invention are vastly superior to known complex bismuth molybdate in terms of producing environmentally acceptable effluents. Thus it will be appreciated that the catalysts of the invention are particularly attractive from a commercial standpoint in that they provide both excellent produce yields (Example 3 and 9 above) and much cleaner waste effluents than known bismuth molybdates.

Although only a few embodiments of the present invention have been described above, it should be appreciated that many modifications can be made without departing from the spirit and scope of the invention. All such modifications are intended to be included within the scope of the present invention, which is to be limited only by the following claims:

We claim:

1. A process for ammoxidizing propylene to produce acrylonitrile wherein propylene, ammonia and an oxygen-containing gas are contacted with an ammoxidation catalyst at elevated temperature to produce said acrylonitrile, said ammoxidation catalyst having the formula:

$$A_aBi_bCe_cW_dMo_fO_x$$

Wherein
A is selected from the group consisting of an alkali metal, Tl, Sm, Ag, Cu, Cr, Sb, Te, Ti, Zr, Th, V or mixtures thereof provided that A must include at least about 0.04 of at least one alkali metal;
a is about .04 to 6;
b is 0.01 to 24;
c is 0.01 to 24;
f+d is 12; provided that both f and d are greater than zero and d is at least about 2;
x is a number sufficient to satisfy the valency requirements of the other elements present;
said catalyst being free of iron and the combination of Te with alkali metal, Tl, Sm, Ag and/or Cu wherein the molar ratio of (Bi+Ce):(W+V+Mo) is in the range from ½ to 5/6 inclusive.

2. A process for ammoxidizing propylene to produce acrylonitrile wherein propylene, ammonia and an oxygen-containing gas are contacted with an ammoxidation catalyst at elevated temperature to produce said acrylonitrile, said ammoxidation catalyst having the formula:

$$A_aBi_bCe_cW_dMo_fO_x$$

wherein

A is selected from the group consisting of alkali metal Tl, Sm Ag, Cu, Cr, Sb, Te, Ti, Zr, Th, V or mixtures provided that A must include at least about 0.04 of at least one alkali metal;

a is about 0.04 to 6;

b is 0.01 to 24;

c is 0.01 to 24;

f+d is 12; provided that both f and d are greater than zero;

x is a number sufficient to satisfy the valency requirements of the other elements present;

said catalyst being free of iron and the combination of Te with alkali metal, Tl, Sm, Ag and/or Cu wherein the molar ratio of (Bi+Ce):(W+V+Mo) is in the range from $\frac{1}{2}$ to 5/6 inclusive.

3. The process of claim 1 wherein d is between about 2 to 4.

* * * * *